United States Patent [19]

Murray

[11] 4,086,497
[45] Apr. 25, 1978

[54] SYSTEM FOR INSPECTING CAN LIDS FOR THROUGH THE LID FLAWS

[75] Inventor: Russell Murray, Laurel, Md.

[73] Assignee: Columbia Research Corporation, Gaithersburg, Md.

[21] Appl. No.: 677,471

[22] Filed: Apr. 15, 1976

[51] Int. Cl.² ............................................. G01N 21/32
[52] U.S. Cl. ................................ 250/562; 250/223 R; 356/201
[58] Field of Search ............... 250/359, 571, 572, 562, 250/563, 223 R, 223 B; 356/200, 201, 204, 205, 237

[56] References Cited

U.S. PATENT DOCUMENTS

| | | | |
|---|---|---|---|
| 3,340,400 | 9/1967 | Quittner | 356/237 |
| 3,807,877 | 4/1974 | Yee | 356/205 |
| 3,991,882 | 11/1976 | Fahnestock et al. | 356/237 |
| 3,994,590 | 11/1976 | Di Martini et al. | 356/205 |
| 4,002,823 | 1/1977 | Van Oosterhout | 250/223 B |

Primary Examiner—David C. Nelms
Attorney, Agent, or Firm—David H. Semmes

[57] ABSTRACT

A method for detecting light passing flaws in discrete elements, which are normally opaque to visible light, characterized by a sampling technique to enhance the signal to noise ratio of the ultimate signal. The ultimate signal is a composite signal generated by the addition of a number of discrete sample signals, each signal representing both a repeating reaction of a photosensitive means to light passing through flaws in the normally opaque element, and random ambient signal noise.

12 Claims, 5 Drawing Figures

SYSTEM FOR INSPECTING CAN LIDS FOR THROUGH THE LID FLAWS

BACKGROUND OF THE INVENTION

(1) Field of the Invention

At the present state-of-the-art, can lids are tested for leaks on a helium tester, such as that made by the Varian Company, by sampling a given number of lids per hours, say approximately 50, from each press. From this sampling, testing is done manually on the selected lids to statistically determine if there are leaks in the overall press run. This is a fairly unreliable technique, since the sample is necessarily small with respect to a normal manufacturing rate of about four lids per second on each station. Since there are conventionally two stations per press, each press outputs about 28,800 lids per hour. Often as a result of this poor sampling technique, many leaking can end elements are passed without being found. Some of these leaking end elements may be found once they are installed as the bottom of a three piece can by subsequent testing. Significantly, however, others are never found because they are used as lids and, as such, the lids cannot be tested after the product is put inside.

Unlike prior art sampling techniques, the present invention teaches a new technique for inspecting each of the can lids while still on the press upon which they are manufactured. The present invention teaches a method and an apparatus for inspecting the can lids as they lie directly within a conveyor belt which moves away from the dies of the press, towards chutes which convey the lids to the subsequent packing region.

2. Description of the Prior Art

In addition to the above description of can lid sampling, the use of the continuous testing techniques have been taught by prior patents. Specifically, Linderman, et al., U.S. Pat. No. 3,416,659, of common assignment with the present invention, illustrates a technique for testing assembled cans which are continuously conveyed upon a belt through a photosensitive testing station. In our prior patent, a constant light source is used to illuminate the outside of a finished can assembly, and as such represents the previously referred to technique of determining leakage in a can end element once it is assembled as the bottom part of a semi-finished can. While this prior patent teaches using a light source emmitting light energy in the visible spectrum, the light source is maintained on as a can is passed through a testing zone. Unlike the present invention, this prior patent employs a modulated light source with a band-pass filter in order to screen out spurious signals. According to the present invention, there is no filtering element for discriminating between frequencies of impinging light, rather by providing a series of repetitive light impingements onto the can lid, the need for light filtering and band-pass filter devices is obviated, as will be explained hereinafter. Another prior art patent disclosing a system for detecting openings in opaque objects is the patent to Trimble et al., U.S. Pat. No. 3,826,923. Trimble employs a radiation source of extremely high intensity, further having a wave length of about 2,000 to 4,000 Angstroms. Trimble therefore employs extremely short wave length radiation for the purpose of penetrating sub-micron openings within an article to be tested, without penetrating through the walls of the article. It is significant that Trimble requires a radiation source in such a particular short wave length and further that the radiation source must be of extremely high intensities and not simply an intermittent radiation of light in the visible spectrum, as is taught herein. Categorically, the prior art represented by Trimble is not operable with a light source having a wave length in the visible spectrum, but rather requires a radiation admission of sufficiently short wave length to pass through an opening of about 300 millimicrons.

Unlike these representative prior art patents, the present invention may employ light in the visible frequency ranges, and depends upon a repetitive light impingement, together with an electronic circuitry for summing the responses of a photosensor system, so that the signal to noise ratio will be vastly improved. In neither of these representative prior art patents is there recognition that a repetitive flashing, for durations as short as 1/500 of a second, can be thereafter summed to improve the signal to noise ratio of the processed signal. Unlike these prior art testing techniques, the present invention recognizes that noise, which will normally be present in any photo-electric signal, is of a purely random nature. The present method takes advantages of the random nature of noise through a series of repetitive samplings which are then summed to significantly improve the signal to noise ratio. Because of the improvement obtained by the repetitive sampling technique, the use of significantly lower energy sources is possible.

SUMMARY OF THE INVENTION

It is therefore an object of the invention to provide a method for accurately detecting the presence of a hole within a light-opaque material, by a series of repetitive light impingements.

It is a further object of the present invention to eliminate the need for critical wave lengths in the light sources being employed, and also to obviate the need for band-pass filters and light frequency discriminating filters in order to accurately discriminate between a signal and the attendant noise level concomitantly generated and to allow the use of a much lower power light source.

The present method employs a light source mounted on one side of a can end lid and a photosensitive means mounted on the other side of the lid as it is conveyed along a belt. According to the present invention either the light source or the photosensitive means, or both, is triggered on and off during the period when the lid is positioned directly between the light source of the photosensitive means. The present method therefore does not interpose any light filtering medium between the can lid and the photosensor device, but rather sums the series of signals generated by the photosensitive means in a subsequent signal processing unit to automatically differentiate between a noise signal and a signal representing a flaw in the can lid.

Other details and advantages of the present method may further be seen with reference to the following description of a preferred embodiment together with the accompanying drawings:

DESCRIPTION OF THE PREFERRED EMBODIMENT

The present method includes a photosensor system for impinging a short duration light pulse onto a can lid to be inspected. The inspecting device itself may consist of a stroboscopic light source positioned above the belt containing the lids to be inspected, with a photosensor unit positioned therebelow. This arrangement is depicted schematically in FIG. 1. Aternatively, the photosensor may be positioned above the moving belt containing the lids for optical inspection, with the light source positioned below, as further schematically illustrated in FIG. 2.

Figure 3:
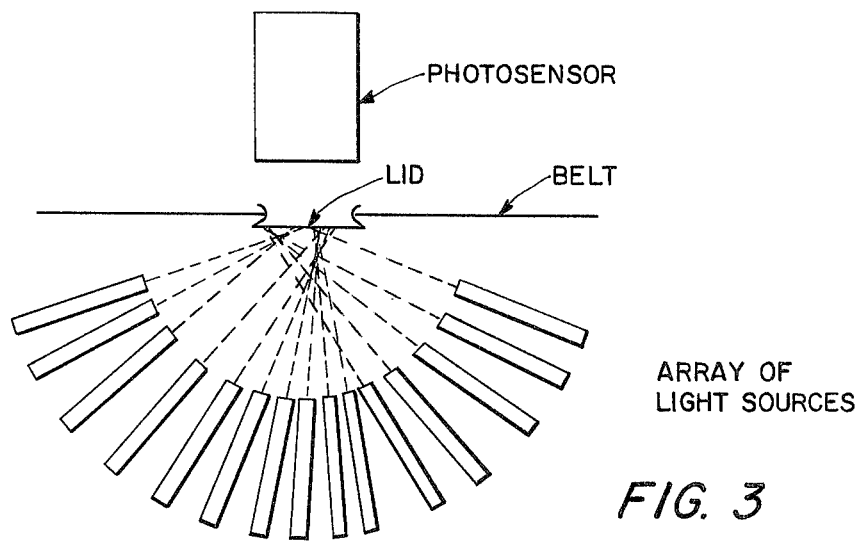
FIG. 3 is a schematic illustration of a third positioning of the photosensor system within the present method.

It is further contemplated, within the present method, that more than one light source may be arranged on either side of the belt carrying the lids to be inspected, with any type of photosensor positioned on the opposite side. A photosensor system, which is usable according to the present method, is schematically illustrated in FIG. 3. While FIG. 3 illustrates the light sources to be arrayed for various angles of incidence to one surface of the lid to be inspected, it is contemplated that, alternatively, the present method can be practiced with a similar array of photosensors, with analogy to the array of light sources as illustrated in FIG. 3.

Figure 1:
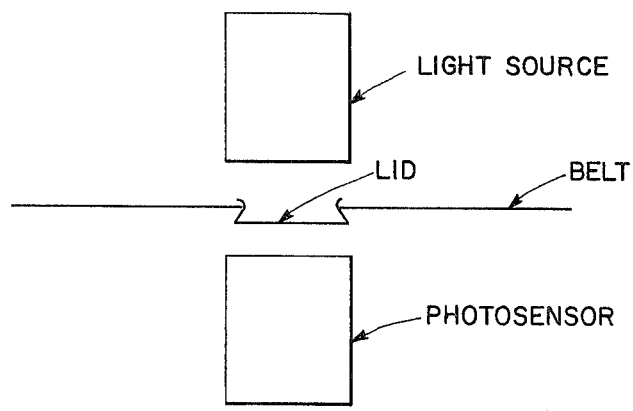
FIG. 1 is a schematic illustration of a first positioning of the photosensor system within the present method.
Figure 2:
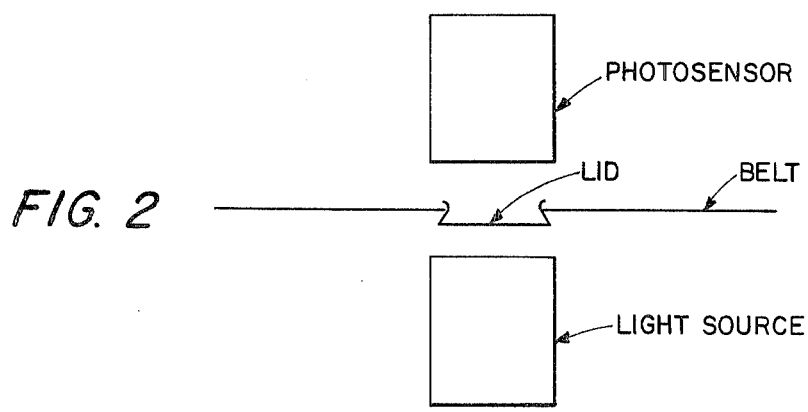
FIG. 2 is a schematic illustration of a second positioning of the photosensor system within the present method.

Therefore, it is simply required, according to the present method that the inspecting device consist of a stroboscopic light source mounted on one side of the can end lid with the photosensitive means mounted on the otherside of the lid. The belt, schematically illustrated in FIGS. 1-3, may further be blackened to render it less reflective to the visible light spectrum emitted by the stroboscopic light source. It should be noted that the present method does not require the use of a light source emitting light in any particular frequency, insofar as the radiation employable herein need only be that visible light as would be produced by a high speed electronic strobe unit. Such high speed electronic strobes are conventionally known, in photographic applications, and such stroboscopic lights are capable of being flashed for durations as short as 1/50,000 of a second. On this point, the elements represented in FIGS. 1, 2 and 3 represent available components for practicing the method which will be hereinafter more particularly explained. For example, the light emitted by the stroboscopic light source may further be collimated to impinge directly upon the lid as it stops at the photosensing station, to minimize light leakage problems between the lid and the holders within the belt. In this respect, as schematically illustrated in FIGS. 1-3, the lid is conventionally of a planar configuration including a flange structure, about its circular periphery, that is engageable within a corresponding aperture of the belt. The light tightness of the holding action between the lid and the belt is not particularly critical according to the successful practice of this method, insofar as the stroboscopic light source will not be triggered until the lid is positioned exactly at the sensing station. In other words, by focusing the burst of light from the light source substantially onto the area defined by the can lid end, the possibility of light leaking between the belt and the lid is minimized. Because the light is triggered on only when the lid is directly below the photosensor, there will be no high level of light on either side of the belt which would tend to reflect between the lid and the belt as it is moved into the sampling position. As a alternative to the light focusing system, a seal can be placed around the rim of the lid between the lid and the photosensitive means to eliminate any light coming around the lid.

According to the present method, either the light source or the photosensitive means, or both, should be triggered on and off so that inspection occurs only when the lid is positioned directly between the light source and the photosensitive means.

According to the preferred embodiment the stroboscopic light source is actuated only when the can lid end is directly positioned at the testing station. Further, according to the preferred embodiment the light source is preferably simply a stroboscopic electronic light source. Alternatively, the stroboscopic light source may be a pulsating laser or an array of conventionally available solid state laser devices. As shown at FIG. 3 the light source can be provided in an array to have an angle of incidence to the can lid from as many angles as possible. Ideally, of course, an array would approach an infinite number of angles of incidence upon one side of the lid, although according to the present invention it has been found that even a focused single light source results in successful practice of the invention taught herein. It is contemplated that in manufacturing operation, it will be advantageous to eliminate any light source which impinges nearly parallel to the belt which carries the lid, thusly minimizing the possibility of light leakage around the flanged end of the can end lid at its interface with the aperture in the belt. Notwithstanding this consideration, either the light sources or the photosensors, or both, may be arranged in arrays to gain detection of holes at the steep angles to the face of the lids to be inspected.

Figure 4:
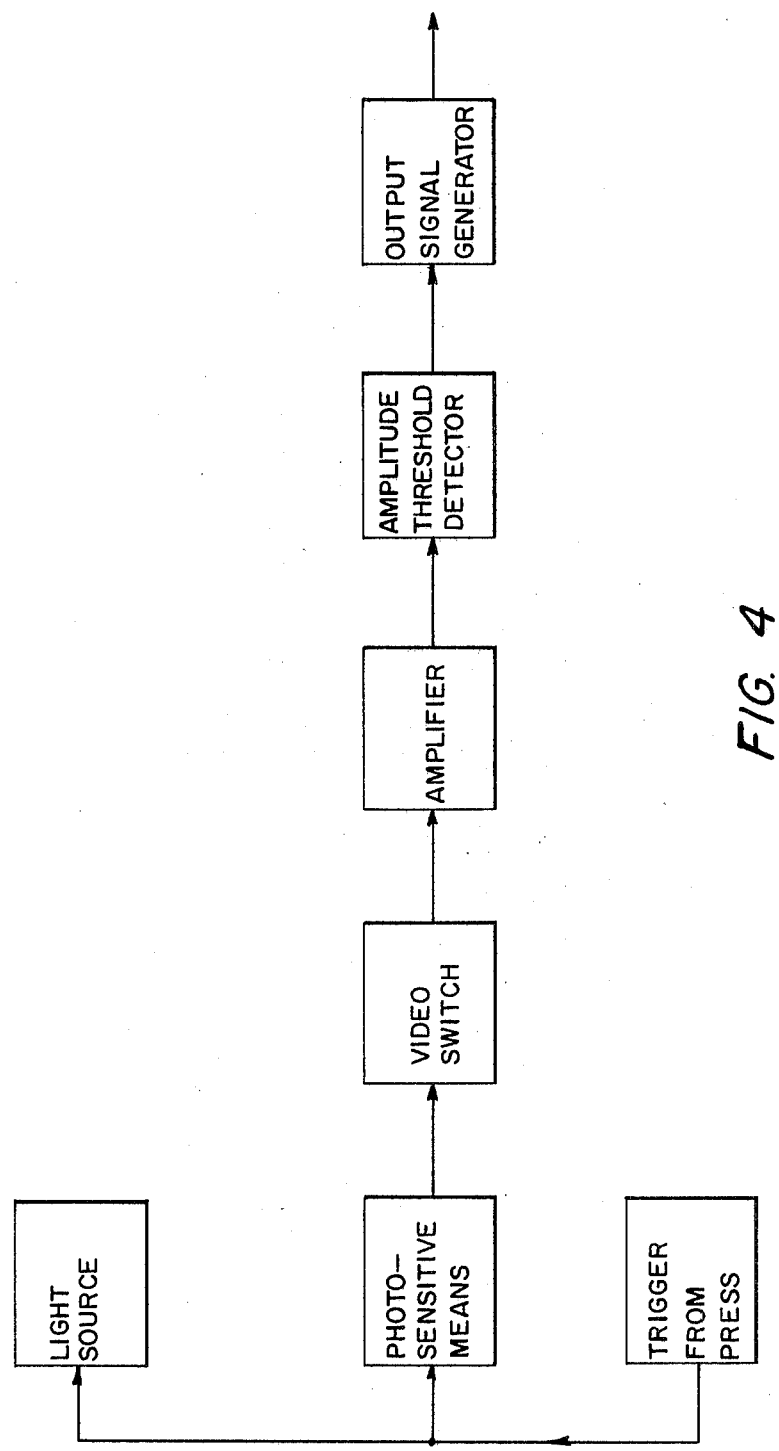
FIG. 4 is a schematic representation of the basic signal processing method according to the present invention.

Having described the basic photosensor systems usable for practice of the present invention, the inventive features of the present method will be hereinafter more particularly described. With reference to FIG. 4, a light source and photosensitive means is shown schematically positioned with the basic circuitry required for the practice of the present method. The light source, according to FIG. 4 will be flashed, for a relatively short duration, only when the lid reaches the proper position at the inspection station. As shown in FIG. 4, there is a trigger mechanism from the press to indicate the presence of the can lid at the sampling station, so that the photosensitive means and the stroboscopic light source are enabled at this point in time to allow any light passing through the lid to generate a signal within the photosensitive means. The photosensitive means, referred to herein, is of conventional structure, and details of this construction need not be further described. Such photosensitive means as photo-multiplier tubes are manifestly described in the prior art, as incorporated above in the description of the prior art.

As is well known, a beam of light passing through a perforation in the can lid end will generate a signal in the photo multiplier tubes, located within the photo sensor, with each signal having a frequency which depends on the modulation frequency of the light and an amplitude which is proportional to the amount of light passing through the material. As shown in FIG. 4, the thusly generated signal may be passed through a video switching device and an amplifier to produce an amplified signal more readily processable by the subsequent electronic circuitry. In this respect, amplification of a signal from a multiplier tube is conventional, per se, as illustrated by another prior patent, of common assignment to the instant invention Murray, et al., U.S. Pat. No. 3,700,909. As shown in FIG. 4, the amplified signal is then directed into an amplitude threshold detector, which functions as a further form of signal processor to change the signal to a pulse form, while maintaining its amplitude information. Such amplitude threshold detectors are also, well known, and details of such an amplitude threshold detector are incorporated herein by reference to our prior patent, U.S. Pat. No. 3,700,909.

Figure 5:
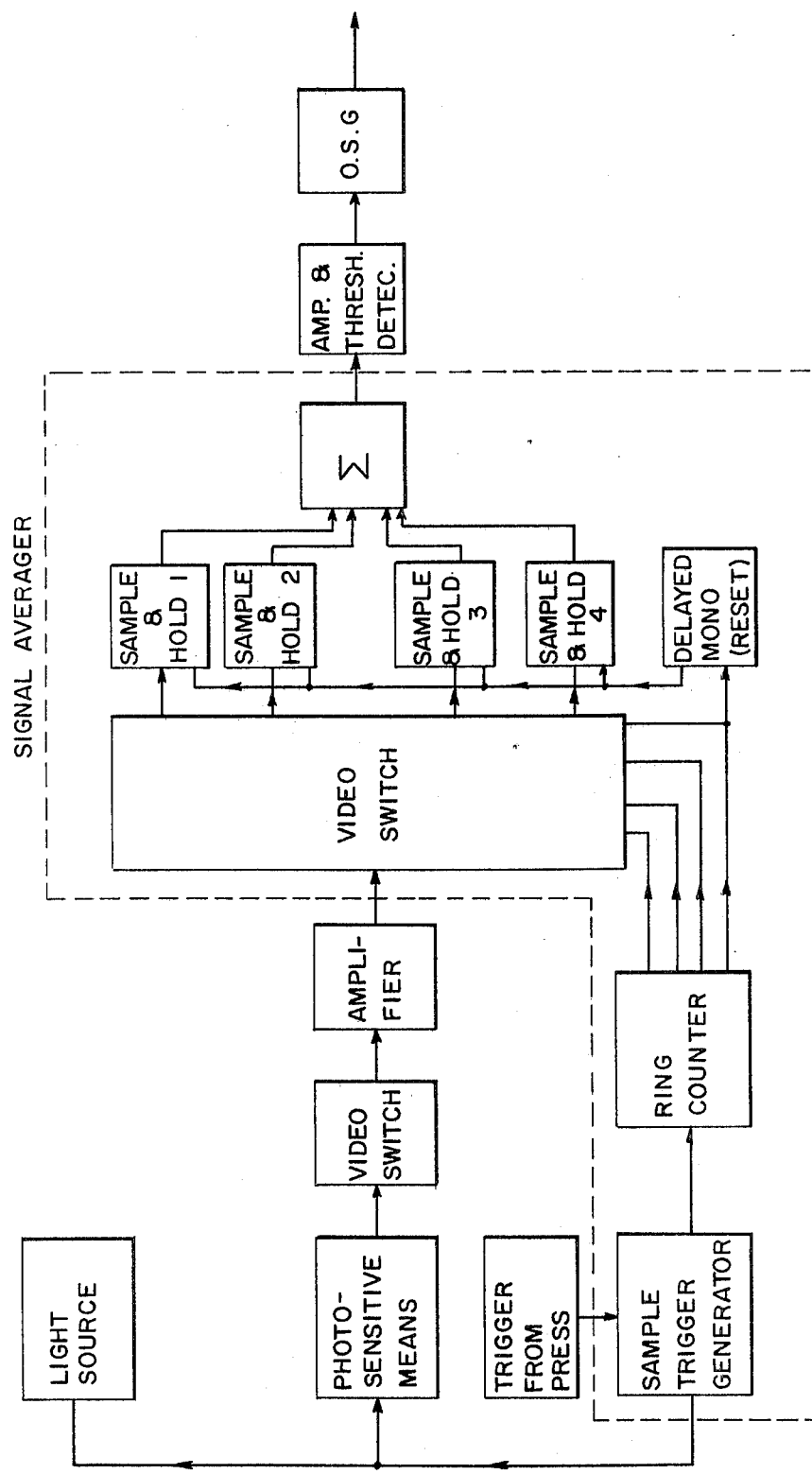
FIG. 5 is a schematic representation of the overall method according to a preferred embodiment of the present invention.

According to the present method, any form of amplitude threshold detector may be usable, and one basic type which shows promising results involves an amplitude threshold detector which will form an inputted amplified signal into a simple pulse. At this point the pulse formed in the amplitude threshold detector is affected by the noise attendant to the prior light sensitive measurement and the associated electronics. At this point FIG. 4 represents the simple representation of generating a signal from a single sampling of a can lid, and as such FIG. 4 represents circuitry capable of only employing one sampling of light transmission through a particular can lid end. With reference to FIG. 5, a preferred embodiment is illustrated, wherein four light samplings are accomplished for given can lid, and as such represents a preferred embodiment of the present method.

In FIG. 5, the method is illustrated wherein a sampling technique is added to the basic electronics of FIG. 4 to make detection of flaws more likely if response to the light is very small and, therefore, practically the same amplitude as the noise. With respect to FIG. 5, the stroboscopic light source would be flashed several times while a single can lid is stopped at the inspection station point of the belt travel. For this purpose, as has been discussed, high-speed electronic strobes, which can be easily flashed for durations as short as 1/50,000 of a second, are effective. The light source may be flashed repetitively while the can lid is at the testing position, so that several samplings of any light coming through the can lid can be measured by the photosensitive means, and subsequently processed as an electronic signal. As shown in FIG. 5 a signal averaging circuitry is illustrated for 4 samplings per given can lid, although it is contemplated within the present method that additional sampling and holding circuits may be easily employed. The present invention, therefore, analyzes discrete each discreet signal generated by the photosensitive means, and includes memorizing these signals and then subsequently summing the signals to dramatically increase the signal to noise ratio of the final signal delivered to a threshold detector. Therefore, the present invention is predicated upon the fact that noise, which will be present in the generation of any signal by the photosensitive means, will be of a purely random nature with respect to subsequent sampling signals. For example, the noise will sometimes be positive and sometimes be negative for a given number of sampling exposures, with the noise having an amplitude which may be higher or lower for any given sampling exposure, with all the characteristics of the noise signal necessarily being on a random basis. For example, if 100 samplings were taken for a given can lid cover, 100 samplings of the noise component should approach zero based upon a simple statistical awareness that the noise has no repetitive characteristics. While noise is entirely random for any given sampling exposure, a similar sampling of 100 exposures upon a can lid containing a hole will create a signal representing the presence of the hole which will be constantly additive. The amplitude of the signal representing the presence of a perforation, or hole, in the can lid is a direct function of the cross-sectional area of the hole, so that the photo multiplier tubes response will include a constant amplitude during all of the exposure samplings. Because there is a repeated constant amplitude generating for each light exposure on the can lid containing a hole, the amplitude of the signal representing the hole will remain constant throughout the number of exposure samplings. These amplitudes representing a hole may then be easily distinguished by adding each of the sampling signals, because the noise portion in each signal will be random.

Again with reference to FIG. 5, each of the signals from the photosensitive means are amplified and directed into a video switching device which selectively switches each subsequent signals into a sampling and holding circuit. As shown, there are four circuits for respectively memorizing the signals from four subsequent light exposures, with appropriate interconnections from the press trigger generator and appropriate resetting circuitry for subsequent can lid testings. The function of the signal averager circuits, therefore, is to store the wave forms from the respective numbers of samplings, shown as 4 in FIG. 5, and then send the thusly sampled signals into a summing junction. The summing junction is a conventional electronic component, and simply takes the respective discrete signals from each of the samples and hold circuitries, and adds them together to produce a composite signal. As has been explained, this resultant signal will show the additive effect of the wave forms for each of the exposure samples, with the constant amplitude representing a perforation in a given can lid appearing in each of the sample signals. While the amplitude of a signal representing a hole will be constant for each sample, the noise component of the signal will be random for each of the samples. Therefore in summing the four signals, as shown in FIG. 5, only the part of the signal representing the presence of a hole will be additively amplified, with the random noise components being cancelled out. The degree of reduction of the noise level, and the consequent increase in the signal to noise ratio, will of course be improved by the number of samples fed into the summing junction, and as an infinite number of exposures are taken the signal to noise ratio would of course be ultimately optimized.

Therefore, a significant aspect of the present method is the improvement of the signal to noise ratio in the resultant signal, with this improved signal to noise ratio not requiring band pass filters and other associated types of discrete signal modifiers. The present method employs the addition of many discrete signals, where each discrete signal includes random noise components. It should be noted that in order to get this sequential sampling of a given can lid, either the sampling time may be close to the duration of a stroboscopic flash, or a single light burst may be discretely analyzed by triggering the photosensitive means during the duration of the burst. In any event, the method taught herein improves the signal to noise ratio of the photomultiplier tube signal by repeated samplings, and the method is not dependent upon whether these samplings are effected by repeated discrete light flashes, or repeated discrete photosensing during a constant light exposure for each lid testing. By using this repeated sampling technique, we have successfully detected leaks, per unit time, with the magnitude of 2 cc of helium leaked at 80 psi of a test pressure. While such a leakage rate is of a relatively small order of magnitude, according to the present method similar leakage rates of 0.5 cc of helium have also been detected through the present method if the hole is relatively straight through the can lid material. Furthermore, according to this method small holes around a tab and rivet assembly of a can lid have been detected with this system, with success having been proved for such defects involving a leakage rate of 2 cc. It is contemplated that the performance of this system may be improved, as necessary, by further controlling the angle of incidence of the light onto the can lid. However, as has been indicated, the present method significantly employs a sampling technique which makes any form of light incidence more likely to result in a processable signal because of the repeated number of exposures, with a subsequent signal summing step.

While a preferred embodiment of the invention has been illustrated herein, applicant intends this invention to be solely limited by the scope of the appended claims:

I claim:

1. A method for detecting light passing flaws within discrete elements, normally opaque to light, characterized by a sampling technique which enhances the signal to noise ratio by generating a composite signal from discrete samplings, comprising the steps of:
   (A) conveying a normally opaque element to a point between a visible spectrum light source and a photosensitive means; and,
   (B) impinging a visible spectrum light beam from said light source onto said normally opaque element at said point and simultaneously energizing said photosensitive means on the other side of said normally opaque element; and,
   (C) generating a first discrete sample signal, in said photosensitive means, in response to said light impingement wherein the amplitude of said first signal is a direct function of the cross-sectional area of a light passing flaw; and
   (D) generating at least one additional discrete sample signal, in said photosensitive means, in response to said light impingement wherein the amplitude of each additional signal is the same direct function of the cross-sectional area of said light passing flaw; and,
   (E) amplifying and then storing the wave forms of said first and at least one additional discrete sample signals; and
   (F) additively summing the wave forms of each of said stored signals to produce a composite signal which represents the addition of the amplitudes of each of said stored signals whereby only the amplitudes representing said light passing flaw in each sample signal will be constantly additive in said composite signal; and
   (G) outputting said composite signal as the enhanced representation of a light passing flaw in said normally opaque element.

2. The method according to claim 1 wherein said step of impinging a light beam comprises generating a light beam in the visible spectrum simultaneously with the arrival of said normally opaque element at said point.

3. The method according to claim 2 wherein said step of impinging a light beam further comprises impinging discrete bursts of light for each of said steps of generating a first, and at least one additional, discrete sample signal.

4. The method according to claim 3 wherein said steps of impinging discrete bursts of light and generating said discrete sample signals are simultaneous.

5. The method according to claim 1 wherein said normally opaque elements comprise circular metal can lid ends and said impinged light is in the visible spectrum.

6. The method according to claim 5 wherein said step of impinging a light beam comprises impinging a stroboscopic light beam simultaneously with the generation of each of said first and at least one additional discrete sample signals.

7. The method according to claim 5 wherein said step of generating said first and at least one additional discrete sample signals comprises dividing the duration of said light impingement into discrete segments for generating each of said signals.

8. The method according to claim 1 wherein at least four discrete sample signals are generated for each normally opaque element being detected.

9. The method according to claim 1 wherein said conveying of a normally opaque element further comprises conveying circular metal can lid ends within correspondingly circular apertures in a continuous belt, said conveying being substantially normal to the direction of said impinging of a light beam.

10. A method according to claim 1 wherein said outputted composite signal is further enhanced by processing in an amplitude threshold detector.

11. A method according to claim 1 wherein said step of storing said first and at least one additional discrete sample signal further comprises amplifying each of said discrete sample signals, subsequently switching each amplified signal into discrete holding circuitry, and simultaneously recalling each held signal for said additive signal summing step.

12. A method according to claim 11 wherein said composite signal is further enhanced by processing in an amplitude threshold detector.

* * * * *